United States Patent [19]
Bracci et al.

[11] Patent Number: 5,857,962
[45] Date of Patent: Jan. 12, 1999

[54] RESECTOSCOPE WITH CURVED ELECTRODE CHANNEL AND RESILIENTLY DEFLECTABLE ELECTRODE SECTION

[75] Inventors: Thomas W. Bracci, Trumbull; Kirsten Doerfert-Pate, Bridgeport; Edward A. Grabover, Brookfield; Naum Metelitsa, Stamford, all of Conn.; Richard P. Muller, Bronx, N.Y.

[73] Assignee: Circon Corporation, Goleta, Calif.

[21] Appl. No.: 816,546

[22] Filed: Mar. 13, 1997

[51] Int. Cl.⁶ ........................................................ A61B 1/00
[52] U.S. Cl. .............................................. 600/105; 600/106
[58] Field of Search ..................................... 600/105, 106, 600/134, 135, 138; 606/45, 46, 47

[56] References Cited

U.S. PATENT DOCUMENTS

| | | | |
|---|---|---|---|
| 4,524,770 | 6/1985 | Orandi | 606/46 |
| 4,538,610 | 9/1985 | Kubota | 128/303.15 |
| 4,648,399 | 3/1987 | Nakada | 128/303.14 |
| 4,919,131 | 4/1990 | Grossi et al. | 606/46 |
| 4,994,062 | 2/1991 | Nishigaki et al. | 606/46 |
| 5,007,907 | 4/1991 | Nishigaki et al. | 606/46 |
| 5,112,330 | 5/1992 | Nishigaki et al. | 606/46 |
| 5,423,813 | 6/1995 | Kaiser et al. | 606/46 |

Primary Examiner—Beverly M. Flanagan
Attorney, Agent, or Firm—Perman & Green, LLP

[57] ABSTRACT

A resectoscope with a working element and an electrode. The working element has a movable actuator assembly with a receiving area for receiving a proximal end of the electrode. The receiving area has an entrance, a plug area, and a curved section between the entrance and the plug area. The electrode has a proximal end with a connection section for connection to an electrical plug connector in the plug area. The proximal end also has a flexible section next to the connection section. The flexible section resiliently deforms along the curved section of the receiving area in the actuator assembly.

21 Claims, 3 Drawing Sheets

RESECTOSCOPE WITH CURVED ELECTRODE CHANNEL AND RESILIENTLY DEFLECTABLE ELECTRODE SECTION

BACKGROUND OF THE INVENTION

1. Field of the Invention

The present invention relates to medical instruments and, more particularly, to a resectoscope, a resectoscope electrode, and connection of the electrode with the resectoscope.

2. Prior Art

U.S. Pat. No. 5,112,330 discloses a resectoscope having an electrode with a flexible cord that is bent inside a sliding part. U.S. Pat. No. 5,007,907 discloses a resectoscope having a curved electrode inserting hole in a slider. A flexible electric cord part of the electrode extends through the hole. U.S. Pat. No. 4,648,399 discloses an electrical connection to an end of an electrode in a slider by an electrical plug. U.S. Pat. No. 4,994,062 discloses an angled electrode hole in a sheath connecting part.

SUMMARY OF THE INVENTION

In accordance with one embodiment of the present invention, a resectoscope is provided comprising an electrode and a working element. The working element has a movable actuator assembly. The actuator assembly has a receiving area for receiving a proximal end of the electrode. The receiving area has an entrance, a plug area and a curved section between the entrance and the plug area. The electrode is removably connected to the working element with the proximal end of the electrode being deformed along the curved section when the electrode is inserted into the receiving area. An electrical connection section of the electrode is located in the plug area of the actuator assembly for removable connection to an electrical plug to be inserted into the plug area.

In accordance with another embodiment of the present invention, a resectoscope electrode is provided having a proximal end for connection to an electrical connector and a distal end. The proximal end of the electrode has a flexible section which is more flexible than an adjacent section.

In accordance with one method of the present invention, a method of connecting an electrode to an actuator assembly of a medical instrument is provided comprising the steps of providing the electrode with a flexible section at a proximal connector end of the electrode; removably inserting the proximal connector end of the electrode into a guide channel of the actuator assembly; bending the electrode at the flexible section along the guide channel; and removably connecting an electrical plug connector to the proximal connector end at a plug receiving area inside the actuator assembly.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
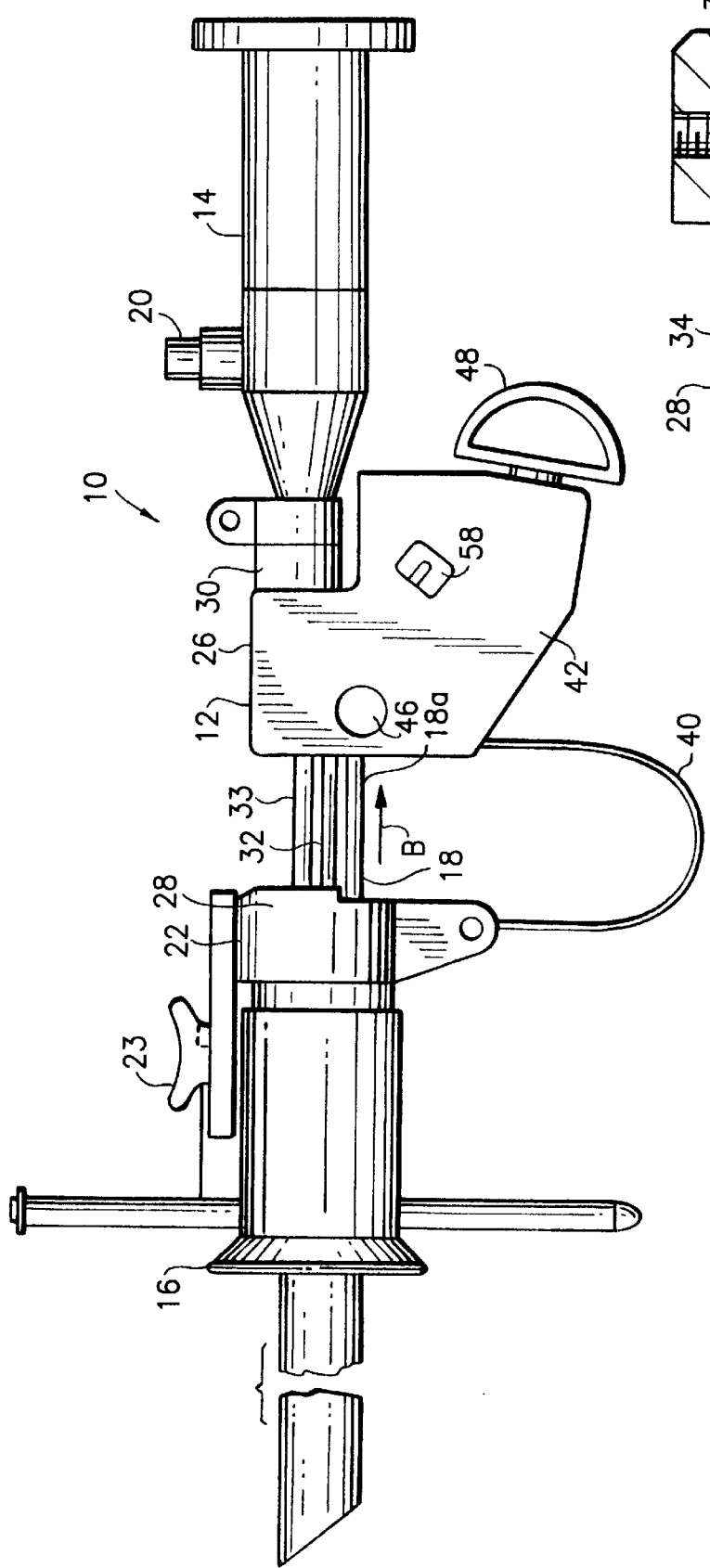
FIG. 1 is an elevational side view of a resectoscope incorporating features of the present invention.

Referring to FIG. 1, there is shown an exploded perspective view of a resectoscope 10 incorporating features of the present invention. Although the present invention will be described with reference to the embodiments shown in the drawings, it should be understood that the present invention can be embodied in many different alternate forms of embodiments. Features of the present invention could be used in other types of endoscopes; other than merely resectoscopes. Electrodes with resilient flexible sections could also be used in other types of endoscopes. In addition, any suitable size, shape or type of elements or materials could be used.

Figure 2:
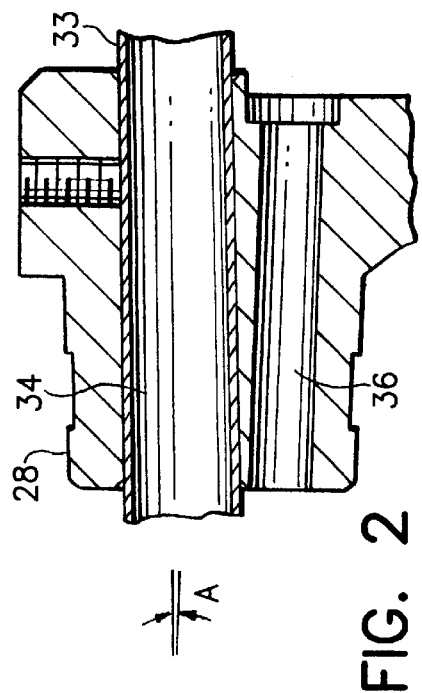
FIG. 2 is a cross-sectional view of the front cone block used in the resectoscope shown in FIG. 1.

The resectoscope 10 generally comprises a working element 12, a telescope 14, a sheath assembly 16 and a throughput device 18 (see FIG. 2). The throughput device is preferably an electrode, but it could also be a device, such as a cold cutting blade or an injection needle. The electrode 18 may have a stabilizer on its front end that slidingly mounts the electrode 18 on the telescope 14. The telescope 14, in the embodiment shown, is a CLASSIC SERIES MAGNAVISION telescope. MAGNAVISION and CLASSIC SERIES MAGNAVISION are trademarks of Circon Corporation of Goleta, Calif. The telescope 14 is removably mounted to the working element 12, and has a connector 20 for connecting fiber optics in the telescope with a light source by means of a flexible light transmitting cable (not shown). The working element 12 generally comprises a frame 22, a movable actuator assembly 26, and a latch assembly 23 for removably mounting the sheath assembly 26 to the frame 22. The telescope 14 and sheath assembly 26 are well known in the art. In alternate embodiments, any suitable type of telescope and/or sheath assembly could be used.

The frame 22 includes a front cone block 28 (see FIG. 2), telescope guide tube 33, a rear block 30, and two parallel bars 32 (only one of which is shown). The bars 32 connect the cone block 28 to the rear block 30. Referring also to FIG. 2, the frame 22 has a telescope channel 34 and the cone block 28 has an electrode channel 36. The telescope guide tube 33 is fixedly located in the cone block 28 which establishes a channel 34 for the telescope. The electrode channel 36 is angled relative to the telescope channel 34 at an angle A. The angle A is about 2°. However, in an alternate embodiment, the angle A could be more or less than 2°. Preferably, the angle A is as close to 0° as possible, i.e.: the electrode remains as close to parallel as possible along the telescope guide tube 33. The telescope guide tube 33, which contains the telescope, extends parallel to and between the two bars 32. In alternate embodiments, other types of frames could be provided.

Figure 3:
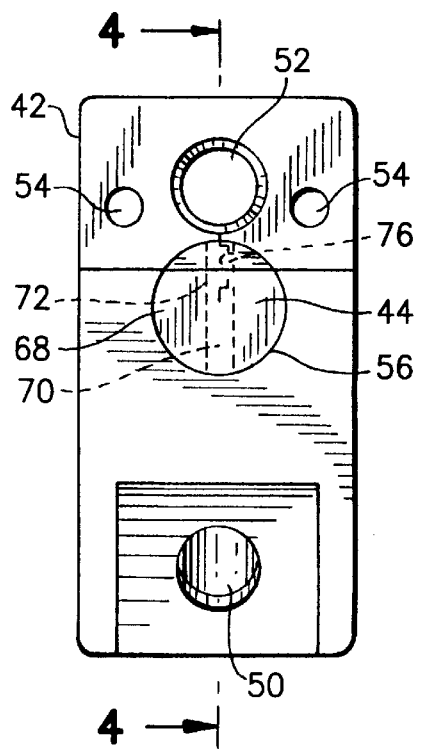
FIG. 3 is a rear end view of the actuator assembly used in the resectoscope shown in FIG. 1.
Figure 4:
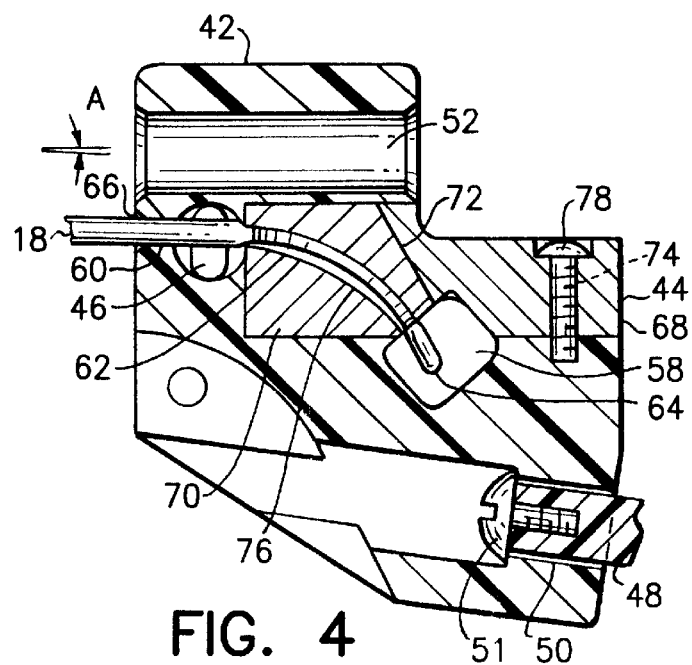
FIG. 4 is a cross-sectional view of the actuator assembly shown in FIG. 3, taken along line 4-4 with an inserted end of the electrode.

The moveable actuator assembly 26 is slidingly mounted on the two bars 32. A spring 40 extends between the cone block 28 and the assembly 26 to bias the assembly 26 in a rearward position against the rear block 30. However, a user can slide the assembly 26 forward on the bars 32, deforming the spring 40, to a forward position against the cone block 28. Other types of movement mechanisms and spring loading are also known in the art. Referring also to FIGS. 3 and 4, the movable actuator assembly 26 includes an actuator block 42, a guide 44, a lock mechanism 46 and a thumb ring 48. FIG. 3 shows the assembly without the thumb ring 48. The thumb ring 48, as seen in FIG. 4 is rotatably mounted to the block 42 at the hole 50 by a fastener 51. Any suitable type of user contact member to move the assembly could be provided. The lock mechanism 46 is generally well known in the art. The lock mechanism 46 is connected to the actuator block 42 and is adapted to retain the position of the electrode 18 in the actuator assembly 26. In alternate embodiments, any suitable type of lock mechanism could be provided.

The actuator block 42 is preferably comprised of a one-piece dielectric member made of a polymer material. The block 42 has an upper section with a telescope hole 52 and two guide bar holes 54. The telescope guide tube 33 extends through the telescope hole 52. The two guide bars 32 extend through the guide bar holes 54. The actuator block 42 is thus slidable on the telescope guide tube 33 and the guide bars 32. The actuator block 42 also includes a guide receiving area 56, a plug receiving area 58 and a portion 60 of an electrode guide channel 62. The plug receiving area 58 is adapted to temporarily removably receive an electrical plug (not shown) for connecting a proximal end 64 of the electrode 18 to a power source. The plug is well known in the art, such as is seen in U.S. Pat. No. 4,919,131, which is hereby incorporated by reference in its entirety. The guide channel 62 has an entrance 66 at the front of the actuator block 42 beneath the telescope channel 52. The portion 60 of the channel 62 is preferably angled at the angle A relative to the channel 52, similar to the angle A in the cone block 28.

The guide 44 is fixedly mounted in the guide receiving area 56 of the actuator block 42. The guide 44 includes a guide housing 68 and a guide insert 70. The guide housing 68 is comprised of a dielectric polymer material similar to the actuator block 42. The guide housing 68 has a front slot 72 and a rear fastener hole 74. The guide insert 70 is preferably harder than the material of the guide housing 68 and the actuator block 42. This allows repeated insertion and removal of electrodes in the guide channel 62 without excessive wear. The insert 70 is suitably sized and shaped to be received in the slot 72 of the guide housing 68. The insert 70 has a curved groove 76 along one lateral side. When the insert 70 is located in the slot 72 of the guide housing 68, the open lateral side of the groove 76 is covered by the housing 68. The housing 68 is inserted in the guide receiving area 56 of the block 42 to stationarily capture the guide insert 70 between the block 42 and the guide housing 68. A fastener 78 fixedly connects the housing 68 to the block 42. However, in alternate embodiments, additional or alternative means to attach the guide 44 to the actuator block could be provided. In an alternate embodiment, the guide 44 need not be provided, such as if the actuator block forms the entire electrode guide channel.

The groove 76 forms part of the guide channel 62. The front of the groove 76 aligns with the rear of the portion 60. The rear of the groove 76 opens into the plug receiving area 58. Thus, the proximal end 64 of the electrode 18 can be inserted through the guide channel 62 from the entrance 66 and into the plug receiving area 58. The guide 44 forms part of the top of the plug receiving area 58. The area 58 is located entirely below the entrance 66 to the guide channel 62 and the area's 58 sides are angled at about 45° relative to the front of the actuator block 42. However, in an alternate embodiment, the plug receiving area 58 need not be located entirely below the entrance 66. Thus, the electrical plug (not shown) is angled for insertion into the area 58 as compared to the non-angled position in the prior art shown in U.S. Pat. No. 4,919,131.

Figure 5:
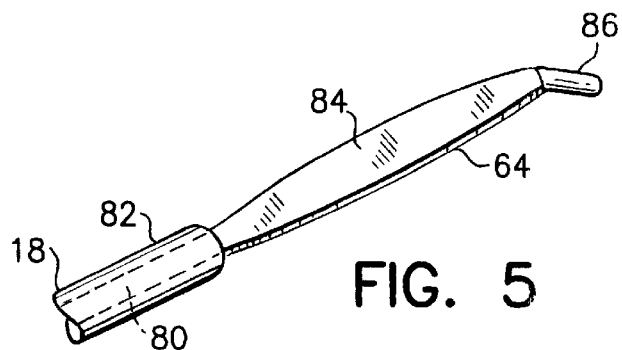
FIG. 5 is a perspective view of the end of the electrode shown in FIG. 4.

Referring now also to FIG. 5, a perspective view of the proximal end 64 of the electrode 18 is shown. The electrode 18 has a main electrical conductor 80 and a dielectric cover 82 along the majority of its length. The main conductor 80 is a relatively rigid wire with a circular cross-section along a majority of its length. The conductor 80 is made of a metal wire similar to standard prior art electrode conductors. The conductor 80 exits the dielectric cover 82 at the proximal end 64. The uniform circular cross-section of the conductor 80 has been deformed at the proximal end 64 to form a flattened section 84 and a bent dog leg section 86. The flattened section 84 extends straight from the rear end of the uniform portion of the conductor 80 and forms a flexible resiliently deformable section. The flexible section 84 is ordinarily straight, but in an alternate embodiment it could have a natural curved or non-straight shape. The bent dog leg section 86 forms a connection section for the electrical plug (not shown) to connect to. The dog leg section 86 is bent relative to the flexible section 84 in order to reduce resistance to insertion of the electrode proximal end 64 through the guide channel 62. However, in an alternate embodiment, the connection section 86 need not be bent relative to the flexible section 84. The connection section 86, in the embodiment shown, has a circular cross-section identical to the section in front of the flattened section. However, in an alternate embodiment, other shapes could be provided. The reason the section 84 has been flattened is to increase its flexibility. The increased flexibility is desired in order to more easily deflect along the curved path of the guide channel 62. However, in alternate embodiments, any suitable means could be used to make the section 84 more flexible than the adjacent sections of the conductor 80, such as cutting grooves in the conductor. The rest of the conductor 80 is preferably retained as relatively rigid, especially in open span length 18a (see FIG. 1), to withstand pushing on the electrode 18 without buckling when the assembly 26 is moved forward. When connecting the electrode 18 to the resectoscope 10, the proximal end 64 of the electrode 18 is passed through the channel 36 in the cone block 28, spans the gap at 18a, and enters into the entrance 66 at the front of the actuator block 42. This is a substantially linear longitudinal insertion up to the entrance, as indicated by arrow B in FIG. 1, with only a slight 2° bend in the front of the cone block 28. However, further rearward longitudinal linear movement of the electrode 18 causes the proximal end 64 of the electrode to move along the curved channel 76 and be bent therealong with its connection end finally protruding into the plug receiving area 58. In an alternate embodiment, the flexible section need not be resilient. However, by providing a section of the proximal end with an increased flexibility, insertion of the proximal end of the electrode into the curved section of the channel 62 is greatly eased.

The present invention provides multiple advantages. In the prior art, the angles A were about 5°. The present invention, because of the reduction in the angles A to about 2°, reduces drag on the electrode 18 as it is moved back and forth when the user moves the actuator assembly 26 back and forth on the guide bars 32. This reduced drag gives the user a better tactile feel of the movement of the electrode 18 when cutting or burning tissue. The present invention allows the angles A to be so much smaller than the prior art by relocation of the plug receiving area 58. The relocation allows the same type of electrical plug to be used as in the prior art and, by movement of the plug receiving area further away from metal components, such as the frame 22 and telescope guide tube 33, potential for inadvertent electrical arcing is reduced. In order to prevent excessive wear on the actuator assembly from repeated insertions and removals of electrodes 18 over a prolonged working life of the resectoscope 10, the proximal end of the electrode 18 has been provided with the flexible section 84 and the bent dog leg 86. This also reduces the insertion force necessary to insert the proximal end of the electrode into actuator assembly, thus, making it easy for the user to connect the electrode even with the curved section of guide channel 62. Furthermore, the flexible section 84 allows the lock mechanism 46 to function properly without excessive force being applied to the lock mechanism from the curving of the proximal electrode end in the channel 62. The use of the guide insert 70, which is made of a relatively hard material, further prevents excessive wear from repeated insertions and removals of electrodes. The guide 44 can also be removed to replace the guide insert 70 if necessary. This is all accomplished, compared to prior art tools, without significantly increasing the overall size of the actuator assembly.

Figure 6:
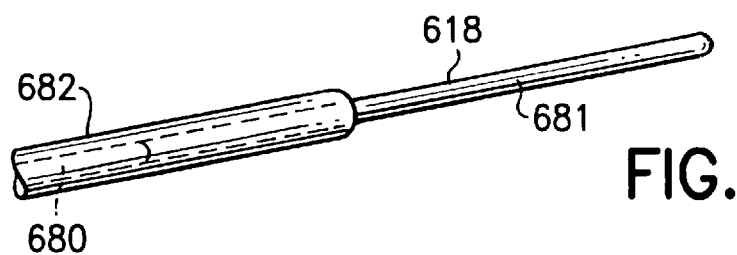
FIG. 6 is a partial perspective view of an alternate embodiment of an electrode for use with the resectoscope shown in FIG. 1.
Figure 7:
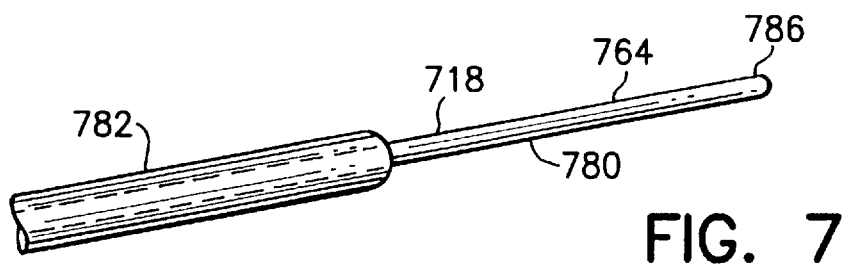
FIG. 7 is a partial perspective view of a second alternate embodiment of an electrode for use with the resectoscope shown in FIG. 1.
Figure 8:
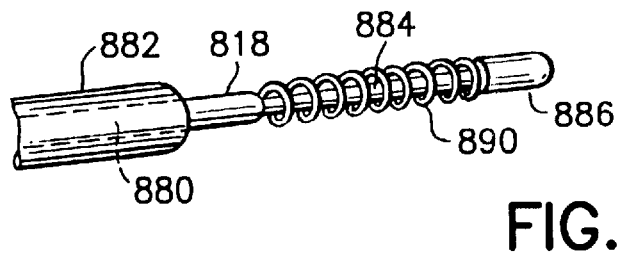
FIG. 8 is a partial perspective view of a third alternate embodiment of an electrode for use with the resectoscope shown in FIG. 1.

Referring now to FIG. 6, an alternate embodiment of the electrode proximal end is shown. The electrode 618 has a main electrical conductor 680, a dielectric cover 682, and an end conductor 681. The main conductor 680 is metal, similar to a main conductor in the prior art. The end conductor 681 is electrically and mechanically connected to the main conductor 680 and is comprised of a shape memory alloy or super-elastic alloy, such as nitinol or tinel. The end conductor 681 is resiliently flexible to relatively easily navigate the path of the guide channel in the actuator assembly. FIG. 7 shows another embodiment of an electrode 718. In this embodiment the electrode includes a single super-elastic alloy conductor 780 and the cover 782. The conductor 780 extends from the proximal end to the distal end of the electrode. Connection section 786 is formed at the proximal end 764. An electrode head (not shown) is attached to a distal end of the conductor 780. Thus, the conductor 780 extends the majority of the length of the electrode. FIG. 8 shows another alternate embodiment of an electrode 818. The electrode 818 has a single main conductor 880, a dielectric cover 882, and a spring 890. The conductor 880 has a thin section 884 in front of the connection section 886. The spring 890 is a coil spring that surrounds the thin section 884. Thus, the thin section 884 and spring 890 form a resiliently deflectable section for the electrode. Other types of flexible sections could be devised by people skilled in the art after reading the above description.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A resectoscope comprising:

an electrode; and a working element having a movable actuator assembly, the actuator assembly having a receiving area for receiving a proximal end of the electrode, the receiving area having an entrance, a plug area and a curved section between the entrance and the plug area, wherein the electrode is removably connected to the working element with the proximal end of the electrode being deformed along the curved section when the electrode is inserted into the receiving area, wherein the curved section terminates in the plug area, and wherein an electrical connection section of the electrode is located in the plug area of the actuator assembly for removable connection to an electrical plug to be inserted into the plug area.

2. A resectoscope as in claim 1 wherein the actuator assembly comprises an actuator block and an electrode guide connected to the actuator block.

3. A resectoscope as in claim 2 wherein the electrode guide comprises material that is harder than material of the actuator block.

4. A resectoscope as in claim 2 wherein the electrode guide is removably connected to the actuator block.

5. A resectoscope as in claim 2 wherein the electrode guide comprises a guide housing and a guide insert.

6. A resectoscope as in claim 5 wherein the electrode guide insert has the curved section of the receiving area along a lateral side thereof.

7. A resectoscope as in claim 6 wherein the electrode guide housing has a slot for receiving the guide insert and the guide housing covers the lateral side of the guide insert to substantially enclose the curved section.

8. A resectoscope as in claim 5 wherein the electrode guide insert is stationarily trapped between the guide housing and the actuator block.

9. A resectoscope as in claim 1 wherein the actuator assembly includes a one-piece polymer actuator block with the receiving area formed therein.

10. A resectoscope as in claim 1 wherein the plug area is located at a relative height on the actuator assembly entirely below the entrance to the receiving area.

11. A resectoscope as in claim 1 wherein the electrode has a substantially resiliently flexible section at the proximal end which is resiliently deformed in the curved section.

12. In a resectoscope electrode having a proximal end for connection to an electrical connector and a distal end, wherein the improvement comprises:

the proximal end of the electrode having a flexible section which is more flexible than an adjacent section, wherein the flexible section comprises a permanently deformed section which has been deformed to increase flexibility relative to the adjacent section.

13. An electrode as in claim 12 wherein the flexible section comprises a flattened section.

14. An electrode as in claim 13 wherein the proximal end has a connection section, located past the flexible section, for connection to an electrical plug connector.

15. An electrode as in claim 14 wherein the connection section is bent at an angle relative to the flattened section.

16. In a resectoscope electrode having a proximal end for connection to an electrical connector and a distal end, wherein the improvement comprises:

the proximal end of the electrode having a flexible section which is more flexible than an adjacent section, wherein the proximal end comprises a flexible shape memory alloy.

17. An electrode as in claim 12 wherein the flexible section is resiliently deflectable.

18. In a resectoscope electrode having a proximal end for connection to an electrical connector and a distal end, wherein the improvement comprises:

the proximal end of the electrode having a flexible section which is more flexible than an adjacent section, wherein the flexible section has a wire core and a spring outer coil.

19. A method of connecting an electrode to an actuator assembly of a medical instrument, the method comprising steps of:

provding the electrode with a flexible section at a proximal connector end of the electrode;

removably inserting the proximal connector end of the electrode into a guide channel of the actuator assembly;

bending the electrode at the flexible section along the guide channel and positioning the proximal connector end into a laterally extending plug receiving area inside the actuator assembly; and removably connecting an electrical plug connector to the proximal connector end at the plug receiving area inside the actuator assembly.

20. A method as in claim 19 wherein the step of bending resiliently bends the flexible section.

21. A method as in claim 19 wherein the step of providing the electrode with a flexible section comprises flattening a portion of the electrode at the proximal connector end.

* * * * *